US006399353B1

(12) United States Patent
Meyers et al.

(10) Patent No.: US 6,399,353 B1
(45) Date of Patent: Jun. 4, 2002

(54) PAPILLOMAVIRUS: BIOSYNTHETIC PROCESS AND ASSAYS

(76) Inventors: Craig M. Meyers, 5724 S. Drexel Ave. #2; Laimonis A. Laimins, 5834 Stony Island, #8C, both of Chicago, IL (US) 60637

( * ) Notice: Subject to any disclaimer, the term of this patent is extended or adjusted under 35 U.S.C. 154(b) by 0 days.

(21) Appl. No.: 08/208,807

(22) Filed: Mar. 10, 1994

Related U.S. Application Data

(63) Continuation of application No. 07/930,648, filed on Aug. 14, 1992, now abandoned.

(51) Int. Cl.$^7$ .............................. C12N 7/00; C12N 7/02; C12N 5/08; C12N 5/10
(52) U.S. Cl. .................... 435/235.1; 435/325; 435/366; 435/371; 435/375; 435/377; 435/384
(58) Field of Search .......................... 435/235.1, 240.2, 435/240.21, 240.23, 240.243, 325, 366, 371, 375, 377, 384, 5, 6

(56) References Cited

U.S. PATENT DOCUMENTS 4,814,268 A    3/1989  Kreider et al. .............. 435/239

OTHER PUBLICATIONS

Aitken, A., Botanical Journal of the Linean Society (1987) 94:247–263.
Asselineau, et al., Exp. Cell Res. (1985) 159:536–539.
Asselineau, et al., Soc. Invest. Dermatol. (1986) 86:181.
Asselineau and Prunieras, Dr. J. Dermatol. (1984) 111 Suppl., 27:219–22.
Ball, et al., J. Biol. Chem. (1978) 253:5861.
Band, et al., Genetics (1990) 87:463–467.
Bedell, et al., J. Virol. (1991) 65:2254.
Bell, et al., J. Invest. Dermatol. (1983) 81:2–10S.
Chamson, et al., J. Cell Biol. (1982) 95:59a.
Christensen, et al., Virology (1991) 181:572–579.
Cullen and Greene, Cell (1989) 58:423.
Dale, et al., Ann. NY Acad. Sci. (1985) 455:330.
Dale, et al., J. Invest. Dermatol. (1987) 88:306.
Davies, et al., J. Virol. (1991) 65:6838.
de Courcelles, et al., J. Biol. Chem. (1985) 260:15762–15770.
Dollard, et al., Genes & Dev. (1992) 6:1131–1142.
Dunn and Ogilvie, J. Ultrastructure Res. (1968) 22:282.
Emerman and Pitelka, In Vitro (1977) 13:316–328.
Evans, et al., J. Natl. Cancer Inst. (1962) 29:277–285.
Favre, et al., J. Virol. (1975) 15:1239.
Freeman, et al., In Vitro (1976) 12:352–362.
Fuchs and Green, Cell (1980) 19:1033.
Fusenig, et al., Bull. Cancer (1978) 65:271–279.
Galloway, D. A., Papillomavirus Report (1990) 1:1–4.
Hasler, et al., Cancer Research (1992) 53:202–208.

Heikkila and Akerman, Biochem. and Biophys. Res. Comm. (1989) 162:1207–1213.
Hurlin, et al., Proc. Natl. Acad. Sci. USA (1991) 88:570–574.
Jarrett, et al., Vet. Rec. (1990) 126:449–452.
Jenson, et al., Pathobiology (1991) 59:396–403.
Jin, et al., Intervirology (1990) 31:345–354.
Kidd, et al., J. Esp. Med. (1936) 64:63–78.
Kopan, et al., J. Cell Biol. (1987) 105:427.
Kreider, et al., J. Virol. (1987) 61:590.
Kreider, et al., Virology (1990) 177:415.
Lapetina, et al., J. Biol. Chem. (1985) 260:1358–1361.
Laurence, et al., Blood (1990) 75:696.
Laverty, et al., Acta Cytol. (1978) 22:195.
Lewis, et al., Rev. Infect. Dis. (1989) 11:s736.
Li, et al., Nature (1992) 356:347.
Lillie, et al., Exp. Cell Res. (1980) 125:153–165.
McCance, et al., Proc. Natl. Acad. Sci. USA (1988) 85:7169.
Meyers and Laimins, Papillomavirus Report (1992) 3:1.
Michalopoulos, et al., Exp. Cell Res. (1975) 94:70–78.
Moll, et al., IBID (1982) 31:11.
Morin and Meisels, IBID (1980) 24:82.
Nelson and Sun, J. Cell Biol. (1983) 97:244.
Olson, et al., Cancer Res. (1962) 22:463–468.
Parker, et al., Mol. Cell Endocrinol. (1989) 65:1–11.
Pfister and Fuchs, Papillomaviruses and Human Disease (Springer–Verlag, Berlin, 1987) p. 1.
Pfister and zur Hausen, Med. Microbiol. Immul. (1978) 166:13–19.
Pfister and zur Hausen, Int. J. Cancer (1978) 21:161–165.
Pilotti, et al., J. Clin. Pathol. (1981) 34:532.
Polyak, et al., J. Virol. (1991) 65:3575.
Rader, et al., Oncogene (1980) 5:571–576.
Regnier, et al. Br. J. Dermatol. (1984) 111 Suppl. 37:223–224.
Stanley, et al., Int. J. Cancer (1989) 43:672–676.
Steinberg, et al., Otolaryngo. Head Neck Surg. (1982) 90:728–735.
Sterling, et al., J. Virol. (1990) 64:6305.
Sugimara, Gann (1982) 73:499–507.
Taichman, et al., The Papovaviridae, The Papillomaviruses, vol. 2 (Salzman and Howley, Eds., Plenum Press, NY, (1987) p. 109.
Viac, et al., J. Invest. Dermatol. (1978) 70:263.
Weinshenker, et al., J. Immunol. (1988) 140:1626.
Woodley, et al., J. Invest. Dermatol. (1982) 79:23–29.

(List continued on next page.)

*Primary Examiner*—David Guzo
(74) *Attorney, Agent, or Firm*—Fulbright & Jaworski LLP

(57) ABSTRACT

The present invention provides a process of biosynthesizing papillomavirus by inducing complete differentiation of an epithelial cell that contains papillomavirus DNA. Complete differentiation is induced by exposing epithelial cells to a protein kinase C inducer. Assays for screening agents that modify papillomavirus biosynthesis, determining the papillomavirus infectivity of epithelial cells, detecting the presence of anti-papillomavirus antibodies and vaccinating against papillomavirus infection are also provided.

10 Claims, No Drawings

OTHER PUBLICATIONS

Wu, et al., Cell (1982) 31:693–703.

Meyers, Biosynthesis of Human Papillomavirus from a Continuous Cell Line Upon Epithelial Differentiation, *Science,* 257:971–973, 1992.

Abstract #47, 1991, Papillomavirus Workshop, Jul. 20–26, 1991, Wilson et al.*

Abstract #419, 1991 Papillomavirus Workshop, Jul. 20–26, 1991, Dollard et al.* deVilliers, "Heterogeneity of the Human Papillomavirus Group", J. of Virol., Nov. 1989, vol. 63, No. 11, pp 4898–4903.*

* cited by examiner

PAPILLOMAVIRUS: BIOSYNTHETIC PROCESS AND ASSAYS

This application is a continuation, of application Ser. No. 07/930,648 filed Aug. 14, 1992 abandoned.

TECHNICAL FIELD OF THE INVENTION

The present invention relates to a biosynthetic process of preparing papillomavirus and to processes for screening anti-papillomaviral agents, determining the papillomavirus infectivity of epithelial cells, detecting the presence of anti-papillomavirus antibodies, and vaccinating against papillomavirus infection.

BACKGROUND OF THE INVENTION

Papillomaviruses (PV) are important pathogens associated with a variety of neoplasias. Human PV (HPV) types 16, 18, 31, 33, 35, and 51 have been associated with malignant lesions of the anogenital area, and types 6 and 11 are found in benign genital lesions (Syijanen, et al., 1987; Salzman, et al., 1987). Study of the complete viral life cycle has been prevented by the lack of a cell culture system that will permit vegetative viral replication. Human papillomaviruses have been propagated in rodents by either grafting infected tissue under the renal capsule (Kreider, et al., 1987; Kreider, et al., 1990) or under the flank skin (Sterling, et al., 1990) of a nude mouse, but no reproducible permissive in vitro system has yet been described. This is probably a result of the evolution of a viral life cycle that is tightly coupled to the differentiation program of keratinocytes in which virion production is limited to differentiating suprabasal cells (Taichman, et al. 1987).

BRIEF SUMMARY OF THE INVENTION

In one aspect, the present invention provides a process of biosynthesizing papillomavirus in an epithelial cell containing papillomavirus DNA comprising inducing complete differentiation of said epithelial cell. Preferably, inducing complete differentiation comprises the steps of:

a) providing a cell line of epithelial cells that contain papillomavirus DNA;

b) placing the epithelial cells onto a dermal equivalent in an epithelial culture medium to form an organotypic culture;

c) maintaining the organotypic culture under biological culture conditions and for a period of time sufficient for the epithelial cells to attach to the dermal equivalent;

d) placing the dermal equivalent on the surface of the epithelial culture medium so that the epithelial cells are not in direct contact with the medium;

e) inducing the expression of filaggrin or a differentiation-specific keratin in the epithelial cells;

f) maintaining the epithelial cells under differentiation conditions and for a period of time sufficient for the epithelial cells to stratify and differentiate; and g) recovering the papillomavirus from the epithelial cells.

In a preferred embodiment, the papilloma virus is a human papillomavirus such as HPV-6, HPV-11, HPV-16, HPV-18, HPV-31, HPV-33 or HPV-51.

Any epithelial cell that contains or can be infected or transformed to contain PV can be used in a process of the present invention. A preferred epithelial cell line whose cells contain papillomavirus DNA is designated CIN-612. CIN-612 cells are derived from a cervical intraepithelial neoplasia type 1 (CIN 1) lesion that maintains episomal copies of HPV type 31b DNA.

Preferably, filaggrin or a differentiation-specific keratin is induced by intermittently exposing epithelial cells to a protein kinase C inducer. A preferred protein kinase C inducer is a phorbol ester or a diacylglycerol. Even more preferably, a protein kinase C inducer is TPA.

Papillomavirus prepared in accordance with a process of the present invention can be used in assay to detect the presence of anti-papillomavirus antibodies in a sample. Such an assay comprises the steps of:

a) contacting a sample with papillomavirus prepared in accordance with a process of this invention to form a reaction mixture;

b) maintaining the reaction mixture under immunoreaction conditions and for a period of time sufficient for the papillomavirus to immunoreact with anti-papillomavirus and form an immunocomplex; and c) detecting the presence of the immunocomplex and thereby the presence of the anti-papillomavirus antibodies.

In another aspect, the present invention provides a process of identifying a substance for its ability to modulate papillomavirus biosynthesis comprising the steps of:

a) preparing a model system of biosynthesizing papillomavirus;

b) selecting a substance suspected of having the ability to modulate papillomavirus biosynthesis; and c) testing for the ability of said substance to modulate said papillomavirus biosynthesis is said model system.

In a preferred embodiment, the model system is a process of biosynthesizing papillomavirus as set forth above. In accordance with that preferred embodiment, papillomavirus is biosynthesized as set forth above in the presence and absence of a substance suspected of having the ability to modulate papillomavirus biosynthesis.

In another aspect, the present invention provides a process of determining the papillomavirus infectivity of epithelial cells comprising the steps of:

a) placing said epithelial cells onto a dermal equivalent in an epithelial culture medium to form an organotypic culture;

b) maintaining said organotypic culture under biological culture conditions and for a period of time sufficient for said epithelial cell to attach to said dermal equivalent;

c) placing said dermal equivalent on the surface of said epithelial culture medium so that the epithelial cells are not in direct contact with said medium;

d) exposing said epithelial cells to papillomavirus;

e) inducing the expression of filaggrin or a differentiation-specific keratin in said epithelial cells;

g) maintaining said epithelial cells under differentiation conditions and for a period of time sufficient for said epithelial cells to stratify and differentiate; and h) detecting the presence of papillomavirus in said epithelial cells and thereby the papillomavirus infectivity of said epithelial cells.

Epithelial cells, papillomavirus, and means for inducing expression of filaggrin or a differentiation-specific keratin in those processes are the same as set forth above in relation to a process of preparing papilloma virus.

DETAILED DESCRIPTION OF THE INVENTION

I. A Process of Biosynthesizing Papillomavirus

In one aspect, the present invention provides a process of biosynthesizing papillomavirus in an epithelial cell containing papillomavirus DNA comprising inducing complete differentiation of said epithelial cell. Preferably, inducing complete differentiation comprises the steps of:

a) providing a cell line of epithelial cells that contain papillomavirus DNA;
b) placing the epithelial cells onto a dermal equivalent in an epithelial culture medium to form an organotypic culture;
c) maintaining the organotypic culture under biological culture conditions and for a period of time sufficient for the epithelial cells to attach to the dermal equivalent;
d) placing the dermal equivalent on the surface of the epithelial culture medium so that the epithelial cells are not in direct contact with the medium;
e) inducing the expression of filaggrin or a differentiation-specific keratin in the epithelial cells;
f) maintaining the epithelial cells under differentiation conditions and for a period of time sufficient for the epithelial cells to stratify and differentiate; and
g) recovering the papillomavirus from the epithelial cells.

Any papillomavirus (PV) can be biosynthesized by a process of this invention. Papillomavirus infections have been described in humans, cattle, horses, dogs, sheep, rabbits, swine, goats, hamsters, cats, rodents, deer, beaver, coyotes, wolves, bears, elephants, rhinoceros, opossum, armadillos, birds, reptiles, amphibians, and fish. Papillomaviruses have been characterized in cattle, deer, horses, rabbits, dogs, rodents, and birds. Papillomavirus Infections in Animals, *Papillomaviruses and Human Disease*, K. Sytjanen, L. Gissman, L. G. Koss (Eds.)

In a preferred embodiment, a papillomavirus that is biosynthesized by a process of the present invention is a human papillomavirus (HPV). Exemplary and preferred HPV include HPV-6, HPV-11, HPV-16, HPV-18, HPV-31, HPV-33 and HPV-51.

Epithelial cells containing papillomavirus DNA can be obtained from infected subjects, prepared by infecting epithelial cells with PV or transfecting epithelial cells with exogenous PV DNA. Exemplary epithelial cells known to exhibit PV infection include foreskin, endocervix, exocervix, breast ducts, cheek, cells from biopsies of genital intraephithelial neoplasias, cells from biopsies from carcinomas, established epithelial cell lines, skin from any body location, uterine epithelium, vaginal epithelium and the like.

A dermal equivalent and an organotypic culture are well known in the art of culturing epithelial cells. Papillomavirus Report, Oncology Information Service, Univ. of Leeds, Leeds LS2 9JT (1992). The organotypic culture systems (rafts) mimics the in vivo physiology of the epidermis by raising the cells to the air-liquid interface. This has been done by either the recombination of epidermal cells with dermal elements or through the use of a collagen matrix maintained on rigid support. Growing keratinocytes in either of these systems allows for a more complete differentiation program to occur than is observed in monolayer. One of the first method of recombining epidermal and dermal components involved the placement of human skin explants on the reticular aspect of split-thickness sections of pig skin, which had been placed on a stainless steel grid. By day 14, the epithelial cells had stratified and differentiated, displaying the characteristic basal, spinous, granular, and squamous layers. Proof that functioning epithelium had formed came when successful test grafts were made for patients with third degree burns. Later, deepidermised human skin flaps were used in place of pig skin and stratification and differentiation of human keratinocyte cells were also observed.

Other studies have used collagen matrices as the dermal components. In studies by Michalopoulos and Pitot the differentiation of liver epithelial cells was observed on a collagen matrix, which had been raised to the air-liquid interface by allowing it to float on top of the media (Michalopoulos, et al., 1975). The liver epithelium grown in this way not only showed morphological features, by viability and functional features comparable to the in vivo state. Using the same technique, additional studies on mammary epithelium, rat lingual epithelial cells, and mouse epidermal cells (Fusenig, et al., 1980) all showed similar abilities to reproduce differentiation in vitro. Introduction of fibroblasts into the collagen matrix improved the accuracy of the differentiated state in vitro.

The basic technique used by laboratories today was described by Asselineau and Prunieras. Briefly, fibroblasts are mixed with medium and collagen I at 0° C. to 4° C. and then placed into tissue culture dishes and incubated at 37° C. until the solution solidifies. The collagen fibers and the fibroblasts for a lattice (plug) which is used as the dermal equivalent. Epidermal cells are seeded on top of this dermal equivalent, allowed to attach and form a monolayer. The plug is then lifted on to a metal grid, and fed so that the media comes only in contact with the bottom of the grid, maintaining the epidermal cells at the air-liquid interface. During a period of two to three weeks the epidermal cells stratify and differentiate. The collagen plugs are then removed from the metal grids and prepared by standard techniques for histological examination.

Epithelial culture media are well known in the art. Exemplary such media have been described by:

1. Hurlin, P. J. Kaur, P., Smith, P. P., Perez-Reyes, N., Blanton, R. A., McDougall, J. K. (1991). Progression of human papillomavirus type 18-immortalized human keratinocytes to a malignant phenotype. *Proc. Natl. Acad. Sci, USA* 88: 570–574;
   keratinocyte growth medium (KGM) (Clonetics, San Diego);

2. Freeman, A. E., Igel, H. J., Herrman, B. J., and Kleinfeld, K. L. (1976). Growth and Characterization of Human Skin Epithelial Cell Cultures. In Vitro 12:352–62
   Culture mediun. The culture medium consisted of Eagle's minimum essential medium supplemented with 0.1 mM nonessential amino acids, 1 mM sodium pyruvate, 2 mM glutamine, 100 units per ml penicillin, 100 µg per ml streptomycin, and 10% fetal bovine serum (all obtained from Microbiological Associates, Bethesda, Md.).

3. Stanley, M. A., Browne, H. M., Appleby, M. and Minson, A. C. (1989). Properties of a Non-tumorigenic Human Cervical Keratinocyte Cell Line. *Int. J. Cancer* 43:672–676.
   GMEM supplemented with 10% FBS (Imperial Laboratories, Salisfury, UK), 0.1 µg ml hydrocortisone and $10^{-10}$ M cholera toxin (Sigma, St. Louis, Mo.). Epidermal growth factor (EGF, Sigma) at 10 ng/ml was added 24 hr after plating. Cultures were maintained at 37% C in a humidified atmosphere containing 5% CO2 and passaged as described by Stanley and Parkinson (1979).

4. Band, V., Zajchowski, D., Kulesa, V., and Sager, R. (1990). Human papilloma virus DNAs immortalize normal human mammary epithelial cells and reduce their growth factor requirements. Genetics 87:463–467.
   DFC-1(D). α-MEM/Ham's nutrient mixture F-12 (1:1, vol/vol) supplemented with epidermal growth factor (EGF) (12.5 ng/ml), 10 nM triiodothyronine, 10 mM Hepes, 50 µM freshly made ascorbic acid, 2 nM estradiol, insulin (1 µg/ml), 2.8 µM hydrocortisone, 0.1 mM ethanolamine, 0.1 mM phosphoethanolamine, transferrin (10 µg/ml), 2 mM L-glutamine, penicillin (100 units/ml), streptomycin (100 mγ/ml) (all from Sigma), 15 nM sodium selenite (Amend Drugs and Chemical, New York), cholera toxin (1 ng/ml) (Schwartz/Mann), 1% fetal calf serum (J. R. Scientific, Woodland, Calif., or HyClone), bovine pituitary extract (35 µM/ml) (Hammond Cell/Tech, Alameda, Calif.). The pH is 7.4 at 6.5% $CO_2$/93.5% air.

D2. DFCI-1 medium minus fetal calf serum and bovine pituitary extract.

D3. D2 minus EGF, hydrocortisone, insulin, triiodothyronine, and cholera toxin.

5. Steinberg, B. M., Abramson, A. L., and Meade, R. P. (1982). Culture of Human Laryngeal Papilloma Cells in Vitro. *Otolaryngol Head Neck Surg* 90:728–735.

Nutrient Mixture F12 (Gibco) is supplemented with 15% fetal calf serum (Sterile Systems, Inc.), 100 U/ml penicillin and 100 µg/ml streptomycin (Gibco), and 10 µg/ml hydrocortisone (Sigma Chemical Co.). Double strength F12 (2×F12) contains 30% fetal calf serum, 200 U/ml penicillin, 20 µg/ml streptomycin, and 20 µg/ml hydrocortisone.

Preferably, epithelial cells are grown on plastic in the presence of mitomycin C-treated 3T3 J2 cells in E medium: 3 parts Dulbecco's modified Eagle's medium/1 part Ham's F-12 medium/10% fetal calf serum (Hyclone, Logan, Utah); hydrocortisone (0.4 µg/ml) (Calbiochem); 0.1 nM cholera toxin (Schwarz-Mann)/transferrin (5 µg/ml) Sigma)/2 nM 3,3'-triodo-L-Thyronine (Sigma) supplemented with epidermal grown factor (5 ng/ml) and insulin (5 µg/ml; Sigma) (Wu, et al., 1982).

In a preferred embodiment, collagen rafts are made with type 1 collagen (Collaborative Research, Inc. Bedford, Mass.)/10×DMEM medium/buffer (8:1:1) at 4° C. as described by the manufacturer. After addition of 1.5×10⁵ 3T3 J2 cells per ml., 2–3 mls of solution is added to each 35-mm plastic Petri dish, and the collagen allowed to gel at 37° C. Epithelial cells are then seeded onto the collagen rafts at 1.0×10⁶ cells per raft, medium is added, and the cells grown to confluence. At confluence, the collagen rafts are raised onto stainless steel grids such that subsequent feeding occurred from below.

Organotypic (raft) cultures recreate important features, both morphological and physiological, of epithelial differentiation in vitro by raising the cells to an air-liquid interface. This has been accomplished by recombination of epidermal cells with a collagen matrix maintained on rigid support (Meyers, et al., 1992). However, raft cultures have continued to be deficient in the most important aspect of papillomavirus research, the ability to propagate virion.

The epithelial cells are induced to differentiate. One stage of productive infection, the differentiation-specific amplification of episomal viral DNA in the upper layers of the epithelium has been achieved in raft cultures (Bedell, et al., 1991). This was done with a cell line (CIN-612) derived from a cervical intraepithelial neoplasia type 1 (CIN 1) lesion that maintains episomal copies of HPV type 31b DNA. No evidence of virion production was detected with this cell line. Although important for replication studies, the ultimate goal of complete vegetative viral replication in vitro was still lacking. One explanation for this inability to propagate HPV in culture is likely the failure of the raft system to faithfully duplicate all aspects of the differentiation program of epithelial cells to which viral production is closely linked (Asselineau, et al., 1987).

In normal keratinocytes, keratin 10 is expressed throughout the suprabasal layers of the differentiating epithelium (Fuchs and Green, 1982; Wu, et al., 1982; Nelson and Sun, 1983; Kopan, et al., 1987) and filaggrin is generally restricted to the stratum granulosum of the differentiating epithelium (Ball, et al., 1978; Dale, et al., 1985; Dale, et al., 1987). In raft cultures of CIN-612 cells, keratin 10 was only weakly present in the intermediate layers and filaggrin was only weakly expressed in the stratum corneum and occasionally in the upper part of the stratum granulosum.

In accordance with a process of the present invention, differentiation is induced so that filaggrin or a differentiation-specific keratin is expressed in induced cells. The data in Table 1, below, identify such differentiation-specific keratins.

| Keratin Number | Where it is found |
|---|---|
| 1,2 | Kerantinizing epidermis from various body sites |
| 4,5,6 | nonkeratinizing stratified squamous epithelia of man |
| 7,8,18 | diverse simple epithelia |
| 9 | foot sole epidermis |
| 10,11 | epidermis of most body locations |
| 13 | noncornified stratified squamous epithelia |
| 14,15,16,17 | epidermis and cultural keratinocytes, hair follicles and many noncornified strafified epithelia |
| 19 | broad range of epithelial tissue |
| 3,12 | human cornea |

Table 1 is from R. Moll, W. W. Franke, D. L. Schiller, B. Geiger and R. Krepler (1982). The Catalog of Human Cytokeratins; Patterns of Expression in Normal Epithelia, Tumors and Cultured Cells. *Cell* 31:11–24.

A preferred differentiation-specific keratin is keratin 10.

In a preferred embodiment, complete differentiation, the expression of filaggrin or a differentiation-specific keratin, is induced by intermittently exposing epithelial cells to a protein kinase C (PKC) inducer. Inducers of PKC are well known in the art.

Exemplary such PKC inducers are diterpenoid esters including tigliane such as 12-0-tetradecanoylphorbol-13-acetate (TPA), ingenane and daphnane [Aitken (1987). The activation of protein kinase C by daphnane, ingenane, and tigliane diterpenoid esters. *Botanical Journal of the Linnean Society* 94:247–263]; Ingenol [C. M. Hasler, G. Acs, and P. M. Blumberg (1992). Specific Binding to Protein Kinase C by Ingenol and Its Induction of Biological Responses. *Cancer Research* 53:202–208]; teleocidins such as teleocidin, $A_f$ [T. Sugimura (1982). Potent Tumor Promoters other than Phorbol Ester and Their Significance. *Gann* 73:499–507]; teleocidin analogs such as indolactams [J. Heikkila and K. E. O. Akerman (1989). (–)-Indolactam V Activates Protein Kinase C and Induxes Changes In Muscarinic Receptor Functions in SH-SY5Y Human Neuroblastoma Cells. *Biochemical and Biophysical Research Communications* 162:1207–1213] and octylindolactams [K. Irie and K. Koshimizu (1988). Structure-Activity Studies of Indolic Alkaloid Tumor Promoters. *Mem. Coll. Agric.*, Kyoto Univ., 132:1–59]; sn-1,2-Dioctanoyl-sn-Glycerol (C8:0) [E. G. Lapetina, B. Reep, B. R. Ganong and R. M. Bell (1985). Exogenous sn-1,2 Diacylglyerols Containing Saturated Acids Function as Bioregulators of Protein Kinase C in Human Platelets. *Journal of Biological Chemistry* 260:1358–1361]; diacylglycerol kinase inhibitors such as R 59 022 [D. C. de Courcelles, P. Roevens and H. Van Belle (1985). R 59 022, A Diacylglycerol Kinase Inhibitor. *Jour-* nal of Biological Chemistry 260:15762–15770]; thrombin [D. C. de Courcelles, P. Roevens and H. Van Belle (1985). R 59 022, A Diacylglycerol Kinase Inhibitor. *Journal of Biological Chemistry* 260:15762–15770]; $\alpha_1$, -Andrenergic [A. Aitken (1987). The activation of protein kinase C by daphnane, ingenane, and tigliane diterpenoid esters. *Botanical Journal of the Linnean Society* 94:247–263]; $H_1$-histaminergic [A. Aitken (1987). The activation of protein kinase C by daphnane, ingenane, and tigliane diterpenoid esters. *Botanical Journal of the Linnean Society* 94:247–263]; Muscarinic-cholinergic [A. Aitken (1987). The activation of protein kinase C by daphnane, ingenane, and tigliane diterpenoid esters. *Botanical Journal of the Linnean Society* 94:247–263]; $V_1$-Vasopression [A. Aitken (1987). The activation of protein kinase C by daphnane, ingenane, and tigliane diterpenoid esters. *Botanical Journal of the Linnean Society* 94:247–263] and arachidonic acid [P. V. Parker, G. Kou, R. M. Marais, F. Mitchell, C. Pears, D. Schaap, S. Stabel and C. Webster. (1989). Protein Kinase C-A Family Affair. *Mol. Cell Endocrinol* 65: 1–11].

Preferably, a PKC inducer is a phorbol ester such as TPA or a diacylglycerol. Virion production induced by phorbol esters has been described in other systems such as Epstein-Barr virus (Crawford, et al., 1986; Davies, et al., 1991; Li, et al., 1992), Pichinde virus (Polyak, et al., 1991), Rift Valley Fever virus (Lewis, et al., 1989), Cytomegalovirus (Weinshenker, et al., 1988), and Human Immunodeficiency virus (Cullen, et al., 1989; Laurence and Cooke, 1990).

A PKC inducer is preferably added to an epithelial cell culture medium that supports a dermal equivalent to which the epithelial cells are attached. The epithelial cells do not directly contact the medium. In a preferred embodiment, a PKC inducer is added to such a medium for one day, followed by four days of exposure to medium not containing that PKC inducer. This cycle is repeated until the epithelial cells stratify and differentiate.

PV is recovered from the organotypic culture using methods well known in the art. In a preferred embodiment, raft cultures are harvested and virions isolated following a series of low speed and high speed centrifugations. Final purification is achieved by cesium chloride isopycnic centrifugation for 24 h at 135,000×g. Samples positive for PV DNA are then phenol/chloroform extracted, ethanol precipitated and run on a 0.7% agarose gel. The DNA is transferred to a nylon membrane with 0.4 N NaOH, probed with HPV 31b DNA, followed by high stringency washes.

II. Detection of Anti-Papillomavirus Antibodies

Papillomavirus biosynthesized by a process of the present invention can used in an assay to detect the presence of anti-PV antibodies in a sample suspected of containing such antibodies. Such an assay comprises the steps of:

a) contacting a sample with papillomavirus prepared in accordance with a process of this invention to form a reaction mixture;

b) maintaining the reaction mixture under immunoreaction conditions and for a period of time sufficient for the papillomavirus to immunoreact with anti-papillomavirus and form an immunocomplex; and c) detecting the presence of the immunocomplex and thereby the presence of the anti-papillomavirus antibodies.

Methods of detecting immunoreaction products between antibodies and virus are well known in the art. It is well known in the art that papillomavirus infection is typically associated with the production of antibodies. See, e.g. Galloway, D. A. (1990). HPV Serology: An Update. *Papillomavirus Report* 1:1–4. Jarrett, W. F., O'Neil, B. W., Gaukroger, J. M. et al. (1990). Studies on vaccination against papillomaviruses: a comparison opf purified virus, tumor and transformed cells in prophylactic vaccination. *Vet. Rec.* 126:449–452. Christensen, N. D., Kreider, J. W., Kan, N. C., Diangelo, S. L. (1991). The open reading frame L2 of cottontail rabbit papillomavirus contains antibody-inducing neutralizing epitopes. *Virology* 181:572–579. Jenson, A. B., Lim, P. Ghim, S. et al. (1991). Identification of linear epitopes of the BPV-1 L1 protein recognized by sera of infected or immunized animals. Pathobiology 59:396–403. Jin, X. W., Cowsert, L., Marshall, D. et al. (1990). Bovine serological response to a recombinant BPV-1 major capsid protein vaccine. Intervirology 31:345–54. Jablonska, S., Orth, G., and Lutzner, M. A. (1980). Morphology and immunology of human warts and familial warts, in: *Leukaemias, Lymphomas and Papillomas: Comparative Aspects* (P. A. Bachmann, ed.). pp. 107–131, Taylor & Francis, London. Kidd, J. G. Beard, J. W., and Rous, P. (1936). Serological reactions with a virus causing a rabbit papilloma which becomes cancerous. II. Tests of the blood of animal carrying various tumors. *J. Exp. Med.* 64:63–78. Pfister, H., and zur Hausen, H. (1978). Characterization of proteins of human papilloma virus (HPV) and antibody response to HPV 1. *Med. Microbiol. Immunol.* 166:13–19. Pfister, H., and zur Hausen, H. (1978). Seroepidemiological studies of human papilloma virus (HPV) infections. *Int. J. Cancer* 21:161–165. Olson, C., Leudke, A. J., and Brobst, D. F. (1962). Induced immunity of skin, vagina, and urinary bladder to bovine papillomatosis. *Cancer Res.* 22:463–468. Evans, C. A., Gormann, L. R., Ito, Y., and Weiser, R. S. (1962). Antitumor immunity in the SHOPE papilloma-carcinoma complex of rabbits. I. Papilloma regression induced by homologous and autologous tissue vaccines. *J. Natl. Cancer Inst.* 29:277–285.

III. Assay for Identifying Substances Having the Ability to Modulate PV Biosynthesis In another aspect, the present invention provides a process of identifying a substance for its ability to modulate papillomavirus biosynthesis comprising the steps of:

a) preparing a model system of biosynthesizing papillomavirus;

b) selecting a substance suspected of having the ability to modulate papillomavirus biosynthesis; and c) testing for the ability of said substance to modulate said papillomavirus biosynthesis is said model system.

In a preferred embodiment, the model system is a process of biosynthesizing papillomavirus as set forth above. In accordance with that preferred embodiment, papillomavirus is biosynthesized as set forth above in the presence and absence of a substance suspected of having the ability to modulate papillomavirus biosynthesis. The ability of a substance to modify PV biosynthesis is determined by comparing the biosynthesis of PV in the presence and absence of that substance.

IV. Process for Determining the Papillomavirus Infectivity of Epithelial Cells In another aspect, the present invention provides a process of determining the papillomavirus infectivity of epithelial cells comprising the steps of:

a) placing said epithelial cells onto a dermal equivalent in an epithelial culture medium to form an organotypic culture;

b) maintaining said organotypic culture under biological culture conditions and for a period of time sufficient for said epithelial cell to attach to said dermal equivalent;

c) placing said dermal equivalent on the surface of said epithelial culture medium so that the epithelial cells are not in direct contact with said medium;

d) exposing said epithelial cells to papillomavirus;

e) inducing the expression of filaggrin or a differentiation-specific keratin in said epithelial cells;

g) maintaining said epithelial cells under differentiation conditions and for a period of time sufficient for said epithelial cells to stratify and differentiate; and h) detecting the presence of papillomavirus in said epithelial cells and thereby the papillomavirus infectivity of said epithelial cells.

Epithelial cells, papillomavirus, and means for inducing expression of filaggrin or a differentiation-specific keratin in those processes are the same as set forth above in relation to a process of preparing papilloma virus.

V. Vaccine Production

In another aspect, the present invention provides a process of vaccinating against papillomavirus comprising immunizing an animal with an immunogenic preparation that includes an effective immunogenic amount of an inactivated or attenuated papillomavirus prepared in accordance with a biosynthetic process of the present invention.

Methods of preparing viral vaccines are well known in the art.

A. Inactivated Virus Vaccines

The primary requirements for an effective vaccine of this type are complete inactivation of infectivity coupled with minimum loss of antigenicity. Ultraviolet irradiation could accomplish this best but is inapplicable because virus inactivated in this manner is capable not only of expressing the function of those genes that have not received a lethal hit, but also of undergoing multiplicity reactivation. Photodynamic inactivated viral nucleic acids efficiently and irreversibly without damaging viral proteins, which therefore retain full immunogenicity. Beta propiolactone is a potentially useful inactivating agent but has been used only rarely because it is a potent carcinogen. The best reagent for inactivating vira nucleic acid without compromising antigenicity is formaldehyde, but it also has drawbacks: first, it inactivates only viruses that contain single-stranded nucleic acids, and second, care must be exercised to avoid formation of a resistant virus fraction. Because inactivated virus cannot multiply, relatively large amounts of this type of vaccine must be administered so as to provide sufficient antigen.

B. Attenuated Active Virus Vaccines

A second method of immunizing against viral pathogens is by administering attenuated virus strains, antibody to which is capable of neutralizing the pathogen. This is the principle on which Jenner's vaccination procedure against smallpox in 1798 was based. The most commonly used method of producing such attenuated virus strains is by repeated passage of the human pathogen in other host species, which results in the selection of variants with drastically reduced virulence for humans.

Attenuated virus vaccines are effective in very small amounts, since the attenuated virus can multiply. This provides a powerful amplification effect; the viral progeny, rather than the virus in the inoculum, acts as the antigen. The attenuated vaccines also possess the advantage of stimulating the formation of all the correct types of antibody molecules. Since only small quantities of this type of vaccine need to be administered, the virus is usually not purified.

The following example illustrates particular embodiments of the present invention and is not limiting of the specification and claims in any way.

EXAMPLE 1

Biosynthesis of Papillomavirus

CIN-612 cells (obtained from Dr. George Wilbanks, Dept. of Obstetrics and Gynecology, Rush Presbyterian Hospital) were grown on collagen rafts in the presence of mitomycin C-treated 3T3 J2 cells in E medium: 3 parts Dulbecco's modified Eagle's medium/i part Ham's F-12 medium/10% fetal calf serum (Hyclone, Logan, Utah); hydrocortisone (0.4 µg/ml) (Calbiochem); 0.1 nM cholera toxin (Schwarz-Mann)/transferrin (5 µg/ml) Sigma)/2 nM 3,3'-triodo-L-Thyronine (Sigma) supplemented with epidermal grown factor (5 ng/ml) and insulin (5 µg/ml; Sigma) (Wu, et al., 1982).

Collagen rafts were made with type 1 collagen ( Collaborative Research, Inc., Bedford, Mass.)/10×DMEM medium/buffer (8:1:1) at 4° C. as described by the manufacturer. After addition of $1.5 \times 10^5$ 3T3 J2 cells per ml., 2–3 mls of solution is added to each 35-mm plastic Petri dish, and the collagen allowed to gel at 37° C. CIN-612 cells were then seeded onto the collagen rafts at $1.0 \times 10^6$ cells per raft, medium added, and the cells grown to confluence. At confluence, the collagen rafts were raised onto stainless steel grids such that subsequent feeding occurred from below.

Reproducible induction of differentiation occurred when raft cultures were incubated 16 to 24 h, every four days with cell culture medium containing 16 nM TPA. Raft cultures were grown for 16 days then harvested, fixed in paraformaldehyde, embedded in paraffin and sectioned for immunohistostaining.

The expression of keratin 10 and filaggrin, was examined by immunostaining thin sections of paraformaldehyde fixed, paraffin embedded raft tissue with the VECTASTAIN Elite ABC Kit (Vector Laboratories, Inc., Burlingame, Calif.). Immunostaining for keratin 10 and filaggrin was performed using a keratin 10 specific monoclonal antibody (*U.S.A ACCURATE CHEMICAL & SCIENTIFIC CORP.*, Westbury, N.Y.) and a filaggrin specific monoclonal antibody (Biomedical Technologies Inc., Stoughton, Mass.) as the primary antibodies.

In TPA treated CIN-612 rafts keratin 10 was expressed throughout most of the suprabasal layers, including the stratum corneum and a strong expression of filaggrin was observed throughout the stratum granulosum and into the stratum corneum.

In vivo expression of viral late genes is only detected in the highly differentiated suprabasal cells of infected tissue (Pfister, et al., 1987). Using antiserum to the HPV 16 L1 major capsid protein (Bedell, et al., 1991), which cross reacts with the L1 major capsid protein of various HPV types (Bedell, et al., 1991), the production of the L1 major capsid protein in the CIN-612 rafts grown with or without TPA treatment was determined. CIN-612 raft cross-sections were examined by immunostaining with the VECTASTAIN Elite ABC Kit (Vector Laboratories. Inc., Burlingame, Calif.) after treatment with antiserum against the major late capsid protein, L1.

Untreated CIN-612 raft cultures showed no specific nuclear staining with the L1 antiserum, while specific nuclear staining was seen in the stratum granulosum and in the stratum corneum of TPA treated CIN-612 raft cultures. Normal rabbit serum was used as control serum and showed no evidence of staining. The specific nuclear staining observed in TPA treated CIN-612 raft cultures is similar to the staining patterns seen in biopsy tissue of HPV associated cervical intraepithelial neoplasia type 1.

These results show that major late capsid protein production occurs concomitantly with the induction of keratin 10 and filaggrin synthesis in TPA treated raft cultures. Similar results have been obtained in six separate experiments with CIN-612 cells at different passages and with different clonal cell lines.

Raft tissue cross-sections were fixed with glutaraldehyde and stained with uranyl acetate. Electron microscopy of cross sections of raft culture tissue revealed that nuclei in the upper portion of the stratum granulosum and the stratum corneum contained virion particles that were approximately 54 nm in size. Virions were commonly observed in bilobulated koilocytic and dyskeratotic nuclei in which the nuclear chromatin had condensed at the nuclear envelope. At higher magnification the particles could be seen superimposed on heterochromatin, as is often seen in vivo. These particles are not seen in nuclei of untreated CIN-612 raft cultures. Virions approximately 54 nm in diameter were also prevalent in the stratum corneum of raft cultures. These results are reminiscent of virions observed in clinical biopsy material from low-grade lesions (Dunn, et al., 1968; Laverty, et al., 1978; Morin and Meisels, 1980; Viac, et al., 1978; Pilotti, et al., 1981). Similar results have been obtained with material from five separate experiments with different passages of CIN-612 cells.

Because infectious assays have not yet been developed for HPV, we sought to determine if the structures we observed in nuclei of CIN-612 cells were indeed virions. Dot blot hybridization was performed on fractions from a isopycnic gradient purification (Favre, et al., 1975) of HPV 31b virions produced in raft culture and the presence of viral DNA confirmed by Southern blot hybridization.

Eight TPA-treated raft cultures were harvested and virions were isolated following a series of low speed and high speed centrifugations. Final purification was achieved by cesium chloride isopycnic centrifugation for 24 h at 135,000×g. Fractions from the bottom of the gradient through fractions determined positive for HPV 31b DNA by dot blot hybridization were dialyzed and examined by Southern blot hybridization. One-tenth of the fractions were incubated at 50° C. for 2 h in the presence of 25 mM EDTA; 0.5% SDS; 100 mg/ml proteinase K; and carrier DNA. The samples were then phenol/chloroform extracted, ethanol precipitated and run on a 0.7% agarose gel. The DNA was transferred to a nylon membrane with 0.4 N NaOH, probed with HPV 31b DNA, followed by high stringency washes. Positive fractions were uranyl acetate-stained and examined by electron microscopy.

From the copy number standards we estimate the yield of viral particles to be at least 40 million per ml in lanes 7 and 8. Fractions positive for HPV 31b DNA contained viral particles as demonstrated by electron microscopy. The density gradient in fractions where virions were found was between 1.3 h and 1.4 h. Both the presence of HPV DNA, and viral particles within the same fractions suggests that these are complete HPV virions—not empty capsids.

These data show that the addition of 12-O-tetradecanoylphorbol-13-acetate (TPA) to the media of organotypic (raft) cultures increased expression of physiological markers of keratinocyte differentiation and concomitantly induced production of virions. Capsid production was detected in differentiated suprabasal cells. Virions approximately 54 nm in size, were observed by electron microscopy in raft tissue cross-sections in the suprabasal layers. Virions purified through isopycnic gradients were found to contain HPV 31b DNA and exhibited an icosahedral shape similar to that seen by papillomaviruses found in clinical samples.

The foregoing example illustrates particular embodiments of the present invention. One of ordinary skill in the art will readily appreciate that changes, modifications and alterations to those embodiments can be made without departing from the scope and true spirit of the invention.

REFERENCES

1. K. Syijanen, L. Gissman, L. G. Koss, in *Papillomaviruses and Human Disease*, (Springer-Verlag, Berlin, 1987); N. P. Salzman, P. M. Howley, in *The Papovaviridae, The Papillomaviruses Vol. 2* (Plenum Press, New York, 1987).
2. J. W. Kreider, M. K. Howett, A. E. Leure-Dupree, R. J. Zaino, J. A. Weber, *J. Virol.* 61, 590 (1987); J. W. Kreider, S. D. Patrick, N. M. Cladel, P. A. Welsh, *Virology* 177, 415 (1990).
3. J. Sterling, M. Stanley, G. Gatward, T. Minson, *J. Virol.* 64, 6305 (1990).
4. L. B. Taichman and R. F. LaPorta, in *The Papovaviridae, The Papillomaviruses* Vol. 2, N. P. Salzman, P. M. Howley, Eds. (Plenum Press, New York, 1987), p. 109.
5. C. M. Meyers and L. A. Laimins, *Papillomavirus Report* 3, 1 (1992).
6. M. A. Bedell et al., *J. Virol.* 65, 2254 (1991).
7. D. Asselineau, B. A. Bernard, C. Bailly, D. Darmon, M. Pruniéras, *Soc. Invest. Dermatol.* 86, 181 (1986); R. Kopan, G. Traska, E. Fuchs, *J. Cell Biol.* 105, 427 (1987).
8. E. Fuchs and H. Green, *Cell* 19, 1033 (1980); R. Moll, W. W. Franke, D. L. Schiller, B. Geiger, R. Krepler, ibid. 31, 11 (1982); Y. J. Wu et al., ibid. 31, 693 (1982); W. G. Nelson and T.-T. Sun, *J. Cell Biol.* 97, 244 (1983); R. Kopan, G. Traska, E. Fuchs, ibid. 105, 427 (1987).
9. B. D. Ball, G. K. Walker, I. A. Bernstein, *J. Biol. Chem.* 253, 5861 (1978); B. A. Dale, K. A. Resing, J. D. Lonsdale-Eccies, *Ann. N.Y. Acad. Sci.* 455, 330 (1985); B. A. Dale, A. M. Gown, P. Fleckman, J. R. Kimball, K. A. Resing, J Invest. Dennatol. 88, 306 (1987).
10. J. S. Rader et al., *Oneogene* 5, 571 (1990).
11. H. Pfister and P. G. Fuchs, in Papillomaviruses and Human Disease, K.
    Syrjänen, L. Gissman, L. G. Koss, Eds. (Springer-Verlag, Berlin, 1987), p. 1.
12. A. E. G. Dunn and M. M. Ogilvie, *J. Ultrastructure Res.* 22, 282 (1968); C. R. Laverty, P. Russell, E. Hills, N. Booth, *Acta Cytol.* 22, 195 (1978); C. Morin and A. Meisels, ibid. 24, 82 (1980); J. Viac, D. Schmitt, J. Thivolet, *J. Invest. Dermatol.* 70, 263 (1978); S. Pilotti, F. Rilke, G. De Palo, G. Della Torre, L. Alasio, *J. Clin. Pathol.* 34, 532 (1981).
13. M. Favre, F. Breitburd, O. Croissant, G. Orth, *J. Virol.* 15, 1239 (1975).
14. D. H. Crawford and I. Ando, *Immunology* 59, 405 (1986); A. H. Davies, R. J. A. Grand, F. J. Evans, A. B. Rickinson, *J. Virol.* 65, 6838 (1991); Q. X. Li et al., *Nature* 356, 347 (1992).
15. S. J. Polyak, W. E. Rawls, D. G. Harnish, *J. Virol.* 65, 3575 (1991).
16. R. M. Lewis, J. C. Morrill, P. B. Jahrling, T. M. Cosgriff, *Rev. Infect. Dis.* 11, s736 (1989).
17. B. G. Weinshenker, S. Wilton, G. P. A. Rice, *J. Immunol.* 140, 1626 (1988).
18. B. R Cullen and W. C. Greene, Cell 58, 423 (1989); J. Laurence and H. Cooke, S. K. Sikder, *Blood* 75, 696 (1990).

19. D. J. McCance, R. Kopan, E. Fuchs, L. A. Laimins, *Proc. Natl. Acad. Sci. USA* 85, 7169 (1988).
20. Freeman A. E., Igel H. J., Herrman B. J., Kleinfeld K. L., In Vitro (1976) 12:352–62.
21. Regnier M., Prunieras M., Woodley D., *Front Matrix Biol.* (1981) 9:4–35.
22. Woodley D., Saurat J H, Prunieras M., Reigner M. Pemphigoid, J. *Invest. Dermatol.* (1982) 79:23–9.
23. Regnier M., Pautrat G., Pauly G, Prunieras M., *Br. J. Derinatol.* (1984) 111 Suppl 27:223–4.
24. Michalopoulos G., Pitot H. C., *Exp. Cell. Res.* (1975) 94:70–8.
25. Emerman J. T., Pitelka D. R., In Vitro (1977) 13:316–28.
26. Lillie J. H., Maccullum D. K., Jepsen A., *Exp Cell Res.* (1980) 125:153–65.
27. Fusenig N. E., Amer S. M., Boukamp P., Worst K. P. M., *Bull. Cancer* (1978) 65:271–9.
28. Bell E., Merrill C., Solomon D., *J. Cell Biol.* (1979) 65:271–9.
29. Bell E., Sher S., Hull B., Merrill C., Rosen S., Chamson A., et al., *J. Invest. Dermatol.* (1983) 81:2–10S.
30. Chamson A., Finley J., Hull B., Bell E., *J. Cell Biol.* (1982) 95:59a.
31. Asselineau D., Prunieras M., *Br. J Derrnatol* (1984) 111 Suppl 27:219–22.
32. Wu, Y.-J., Parker, M., Binder, N. E., Beckett, M. A., Sinard, J. H., Griffiths, C. T. & Rheinwald J. G. (1982) Cell 31, 693–703
33. Hurlin, P. J. Kaur, P., Smith, P. P., Perez-Reyes, N., Blanton, R. A., McDougall, J. K., *Proc. Natl. Acad. Sci, USA* (1991) 88: 570–574
34. Stanley, M. A., Browne, H. M., Appleby, M. and Minson, A. C., *Int. J. Cancer* (1989) 43:672–676.
35. Band, V., Zajchowski, D., Kulesa, V., and Sager, R., Genetics (1990) 87:463–467.
36. Steinberg, B. M., Abramson, A. L., and Meade, R. P., *Otolaryngol. Head Neck Surg.* (1982) 90:728–735.
37. Aitken, A., *Botanical Journal of the Linnean Society* (1987) 94;247–263; C. M., Hasler, G. Acs, and P. M. Blumberg, *Cancer Research* (1992) 53:202–208; T. Sugimura, Gann (1982) 73:499–507; J. Keikkila and K. E. O. Akerman, *Biochemical and Biophysical Research Communications* (1989) 162:1207–1213; K. Irie and K. Koshimizu, *Mem. Coll. Agric.* (1988) 132:1–59; E. G. Lapetina, B. Reep, B. R. Ganong and R. M. Bell, *Journal of Biological Chemistry* (1985) 260:1358–1361; D. C. de Courcelles, P. Roevens and H. Van Belle, *Journal of Biological Chemistry* (1985) 260:15762–15770; P. V. Parker, G. Kou, R. M., Marais, F. Mitchell, C. Pears, D. Schaap, S. Stabel and C. Webster, *Mol. Cell Endocrinol.* (1989) 65:1–11.
38. Galloway, D. A., *Papillomavirus Report* (1990) 1:1–4.
39. Jarrett, W. F., O'Neil, B. W., Gaukroger, J. M. et al., *Vet. Rec.* (1990) 126:449–452.
40. Christensen, N. D., Kreider, J. W., Kan, N. C., Diangelo, S. L., *Virology* (1991) 181:572–579.
41. Jenson, A. B., Lim, P. Ghim, S. et al., *Pathobiology* (1991) 59:396–403.
42. Jin, X. W., Cowsert, L., Marshall, D. et al., *Intervirology* (1990) 31:345–54.
43. Jablonska, S., Orth, G., and Lutzner, M. A., *Leukaemias, Lymphomas and Papillomas: Comparative Aspects* (1990) (P. A. Bachmann, ed.). pp. 107–131, Taylor & Francis, London.
44. Kidd, J. G. Beard, J. W., and Rous, P., *J. Exp. Med.* (1936) 64:63–78.
45. Pfister, H., and zur Hausen, H., *Med. Microbiol. Immunol.* (1978) 166:13–19.
46. Pfister, H., and zur Hausen, H., *Int. J. Cancer* (1978) 21:161–165.
47. Olson, C., Leudke, A. J., and Brobst, D. F., *Cancer Res.* (1962) 22:463–468.
48. Evans, C. A., Gormann, L. R., Ito, Y., and Weiser, R. S., *J. Natl. Cancer Inst.* (1962) 29:277–285.

What is claimed is:

1. A process of biosynthesizing human papillomavirus in an epithelial cell containing papillomavirus DNA, but not papillomavirus particles, comprising inducing differentiation of said epithelial cell by exposing said epithelial cell to a protein kinase C inducer.

2. The process according to claim 1 wherein said human papillomavirus is HPV-6, HPV-11, HPV-16, HPV-18, HPV-31, HPV-33 or HPV-51.

3. The process according to claim 1 wherein said protein kinase C inducer is a phorbol ester or a diacylglycerol.

4. A process of biosynthesizing human papillomavirus in an epithelial cell, said process comprising the steps of:

a) providing a cell line of said epithelial cells that contain human papillomavirus DNA, but not papillomavirus particles;

b) placing said epithelial cells onto a dermal equivalent in an epithelial culture medium to form an organotypic culture;

c) maintaining said organotypic culture under biological culture conditions and for a period of time sufficient for said epithelial cell to attach to said dermal equivalent;

d) placing said dermal equivalent on the surface of said epithelial cultural medium so that the epithelial cells are not in direct contact with said medium;

e) inducing the expression of filaggrin or a differentiation-specific keratin in said epithelial cells;

f) maintaining said epithelial under differentiation conditions and for a period of time sufficient for said epithelial cells to stratify and differentiate; and g) recovering said papillomavirus.

5. The process according to claim 4 wherein said cell line is designated CIN-612.

6. The process according to claim 4 wherein inducing is intermittently exposing said epithelial cells to a protein kinase C inducer.

7. The process according to claim 4 wherein said human papillomavirus is HPV-6, HPV-11, HPV-16, HPV-18, HPV-31, HPV-33 or HPV-51.

8. The process according to claim 6 wherein said protein kinase inducer is a phorbol ester or a diacylglycerol.

9. The process according to claim 8 wherein said phorbol ester is 12-O-tetradecanoylphorbol-13-acetate.

10. The process according to claim 3 wherein said phorbol ester is 12-O-tetradecanoylphorbol-13-acetate.

* * * * *